United States Patent [19]
Gianotti

[11] Patent Number: 6,068,635
[45] Date of Patent: May 30, 2000

[54] DEVICE FOR INTRODUCING AN ENDOPROSTHESIS INTO A CATHETER SHAFT

[75] Inventor: Marc Gianotti, Wiesendangen, Switzerland

[73] Assignee: Schneider (USA) Inc, Plymouth, Minn.

[21] Appl. No.: 09/090,608

[22] Filed: Jun. 4, 1998

[30] Foreign Application Priority Data

Mar. 4, 1998 [EP] European Pat. Off. ............ 98103804

[51] Int. Cl.⁷ .................................................. A61F 11/00
[52] U.S. Cl. .......................................... 606/108; 606/198
[58] Field of Search .................... 606/108, 198, 606/195, 191; 623/1, 12

[56] References Cited

U.S. PATENT DOCUMENTS

| | | | |
|---|---|---|---|
| 4,512,338 | 4/1985 | Balko et al. | |
| 5,026,377 | 6/1991 | Burton et al. | 606/108 |
| 5,183,085 | 2/1993 | Timmermans | 140/89 |
| 5,290,305 | 3/1994 | Inoue | 606/191 |
| 5,484,444 | 1/1996 | Braunschweiler et al. | 606/108 |
| 5,591,222 | 1/1997 | Susawa et al. | 623/1 |
| 5,626,604 | 5/1997 | Cottone, Jr. | 606/198 |
| 5,630,830 | 5/1997 | Verbeek | 606/198 |
| 5,672,169 | 9/1997 | Verbeek | 606/1 |
| 5,676,671 | 10/1997 | Inoue | 606/108 |
| 5,700,269 | 12/1997 | Pinchuk et al. | 606/108 |
| 5,725,519 | 3/1998 | Penner et al. | 606/1 |
| 5,738,674 | 4/1998 | Williams et al. | 606/108 |
| 5,746,764 | 5/1998 | Green et al. | 606/108 |
| 5,749,921 | 5/1998 | Lenker et al. | 623/1 |
| 5,810,838 | 9/1998 | Solar | 606/108 |
| B1 4,655,771 | 9/1996 | Wallsten | 623/1 |

FOREIGN PATENT DOCUMENTS

| | | |
|---|---|---|
| 0119688A2 | 9/1984 | European Pat. Off. . |
| 0701800A1 | 3/1994 | European Pat. Off. . |
| 0607468B1 | 7/1994 | European Pat. Off. . |
| 0786267A1 | 7/1997 | European Pat. Off. . |
| 96/37167 | 11/1996 | WIPO . |
| 9639077 | 12/1996 | WIPO . |

Primary Examiner—Michael Buiz
Assistant Examiner—Kevin Truong
Attorney, Agent, or Firm—Todd P. Messal

[57] ABSTRACT

The invention relates to a procedure as well as a device for introducing an endoprosthesis into the distal end of a catheter by means of which the endoprosthesis is introduced into a vessel for implantation therein and is released to undergo self expansion by moving the tip of a catheter axially relative to the distal end of an outer catheter. An embodiment of the proposed device comprises a hollow cylindrical housing designed to receive the endoprosthesis, a piston axially displaceable therein which can be brought into engagement with the endoprosthesis, and a nose section arranged at one end of the housing, said nose section being provided with a recess tapering in the direction of an opening, and by means of said recess the endoprosthesis supplied by the piston may be introduced, with compressed diameter and in elongated form, into the distal end of the catheter replaceably arranged on the nose section.

17 Claims, 10 Drawing Sheets

DEVICE FOR INTRODUCING AN ENDOPROSTHESIS INTO A CATHETER SHAFT

DESCRIPTION OF THE INVENTION

This application claims priority under 35 U.S.C. § 119 of European Patent Application No. 98103804.5, filed in the European Patent Office on Mar. 4, 1998.

The invention relates to a device for introducing a tubular, self-expanding endoprosthesis into a catheter shaft.

BACKGROUND OF THE INVENTION

It is common knowledge that self-expanding endoprostheses, of the kind described for example in U.S. Pat. No. 4,655,771, are used to treat vascular disorders. In this case, for example, an endoprosthesis arranged in the lumen at the distal end of a long catheter, which can be introduced into the (blood) vessel to be treated, is released by the catheter at a predetermined position in the vessel.

EP 0 607 468 B1 describes a long catheter for implanting a self-expanding endoprosthesis (stent) in a vessel, said catheter comprising a flexible outer catheter, a flexible inner catheter arranged therein, and a catheter tip connected via an intermediate element with the distal end of the inner catheter to form a loading chamber for the endoprosthesis. In this catheter, while the outer catheter is partially retracted, the endoprosthesis is manually reduced in diameter and introduced into or placed in the loading chamber provided, and the outer catheter is then gradually advanced over the endoprosthesis up to the tip of the catheter.

In addition, WO-A 96/93077 describes a measuring device having the form of a catheter and comprising a sleeve body, a hollow cylindrical piston rod arranged coaxially therein and possessing on its outer periphery a measuring scale, a self-expanding endoprosthesis attached to the distal end of the piston rod and capable of being drawn into the cylindrical inner space of the sleeve body, as well as an inner catheter passing axially through the piston rod, said catheter having a catheter tip at its distal end. Using this device, in a first phase the catheter is introduced into a vessel, while being monitored by X-ray means, in order to determine the length of the endoprosthesis, which is difficult to estimate from outside the body, and the required length of the endoprosthesis is then read off from the measuring scale on the piston rod. Next, the piston rod, with the endoprosthesis attached thereto, is retracted into the sleeve body of the catheter and the device is fully removed from the vessel. In a second phase, an endoprosthesis is cut to the measured length, either the endoprosthesis attached to the piston rod may be cut according to the measurement or another endoprosthesis is cut to length. The endoprosthesis of suitable length must then, however, be reintroduced (loaded) by hand into an insertion catheter, of the kind described for example, in the EP 0 607 568 B1, and it is then implanted by means of this catheter.

In an alternative embodiment, in order to simplify the loading process, the catheter is disassembled in the second phase and the endoprosthesis is drawn forwards through the sleeve body from the proximal end, using the piston rod, until a point marked on the endoprosthesis according to the measurement process projects from the distal opening of the sleeve body. The endoprosthesis is cut off at this point so that the sleeve body is loaded with a section of endoprosthesis of the required length, while the piston rod with the attached remainder of the endoprosthesis is no longer needed. Finally, in order to introduce the endoprosthesis, the catheter is reassembled with the replacement piston rod and the inner catheter.

The purpose of the invention is to create a device by means of which it is possible for an endoprosthesis of preferably predetermined dimensions, which is intended to be implanted in a vessel, to be introduced as rapidly as possible into the distal end of a catheter while maintaining safe and sterile handling conditions.

SUMMARY OF THE INVENTION

The device according to the invention is characterized by a housing for receiving the endoprosthesis, a piston unit for axially displacing the endoprosthesis and a tapering outlet opening in the housing for radially compressing the endoprosthesis.

In sum the present invention relates to a device for introducing a tubular, self-expanding endoprosthesis into a catheter shaft, the device comprising a housing for receiving the endoprosthesis, a piston unit for axially displacing the endoprosthesis and a tapering outlet opening in the housing for radially compressing the endoprosthesis. The housing is of hollow cylindrical design, the piston unit is displaceable therein along the axis of the cylinder, and the outlet opening is arranged coaxially to the axis of the cylinder. The outlet opening has the form of a truncated cone wherein the truncated cone possesses an oblique angle. The outlet opening has the form of a series of adjacent truncated cones and the form of a hyperboloidal section. The outlet opening is arranged in a replaceable nose section of the housing wherein the nose section is replaceable by virtue of being provided with a threaded connection, is divisible, and possesses two parts connected by a joint, said parts being pivotable between an open, replacement position and a closed, locking position. The parts are lockable in the closed position to fasten them on the housing. The piston unit is annular in shape and has an axial recess. The housing possesses a connecting opening, arranged coaxially to the outlet opening, for receiving an end section of the catheter shaft. The outlet opening possesses several sections with stepped diameters. The housing is made at least partially of transparent material and may be opened laterally in relation to the direction of movement of the piston unit to receive the endoprosthesis. The piston unit may be removed from the housing in order to receive the endoprosthesis.

Further advantages and characteristics of the device and details of the invention are apparent from the following patent claims, description, and drawings.

BRIEF DESCRIPTION OF THE DRAWING

Various embodiments of the invention are described below on the basis of the following drawings which have been provided to illustrate but not limit, the present invention.

DESCRIPTION OF THE PREFERRED EMBODIMENT

Figure 1:
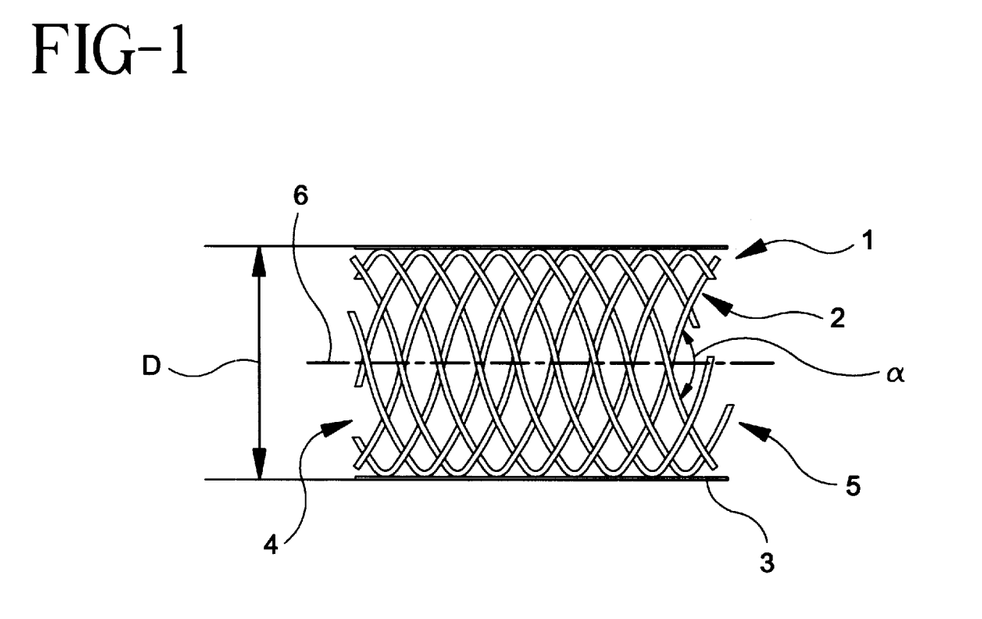
FIG. 1 a lateral view of part of a radially expanded endoprosthesis.
Figure 2:
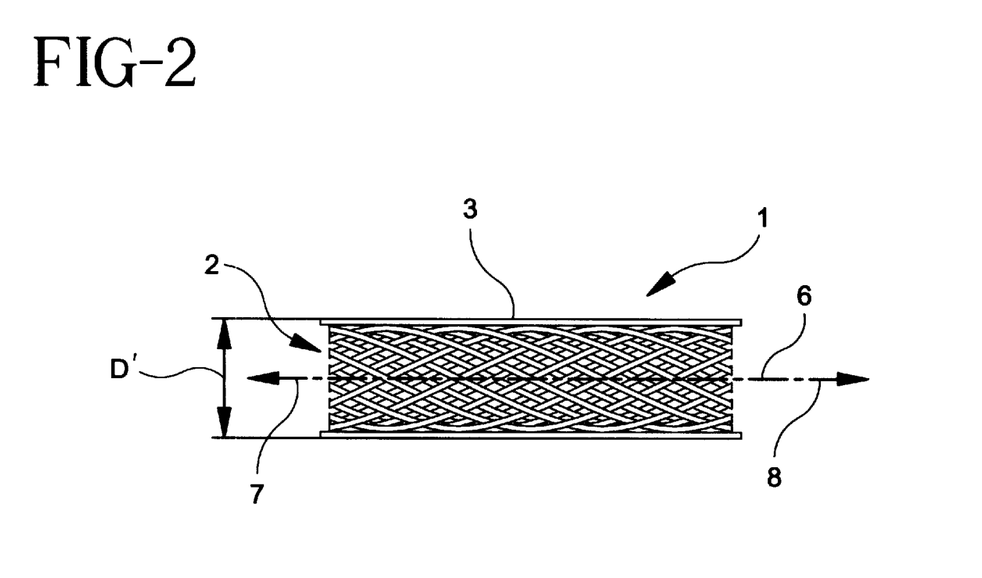
FIG. 2 the endoprosthesis shown in lateral view in FIG. 1, depicted here in the axially extended state.
Figure 3:
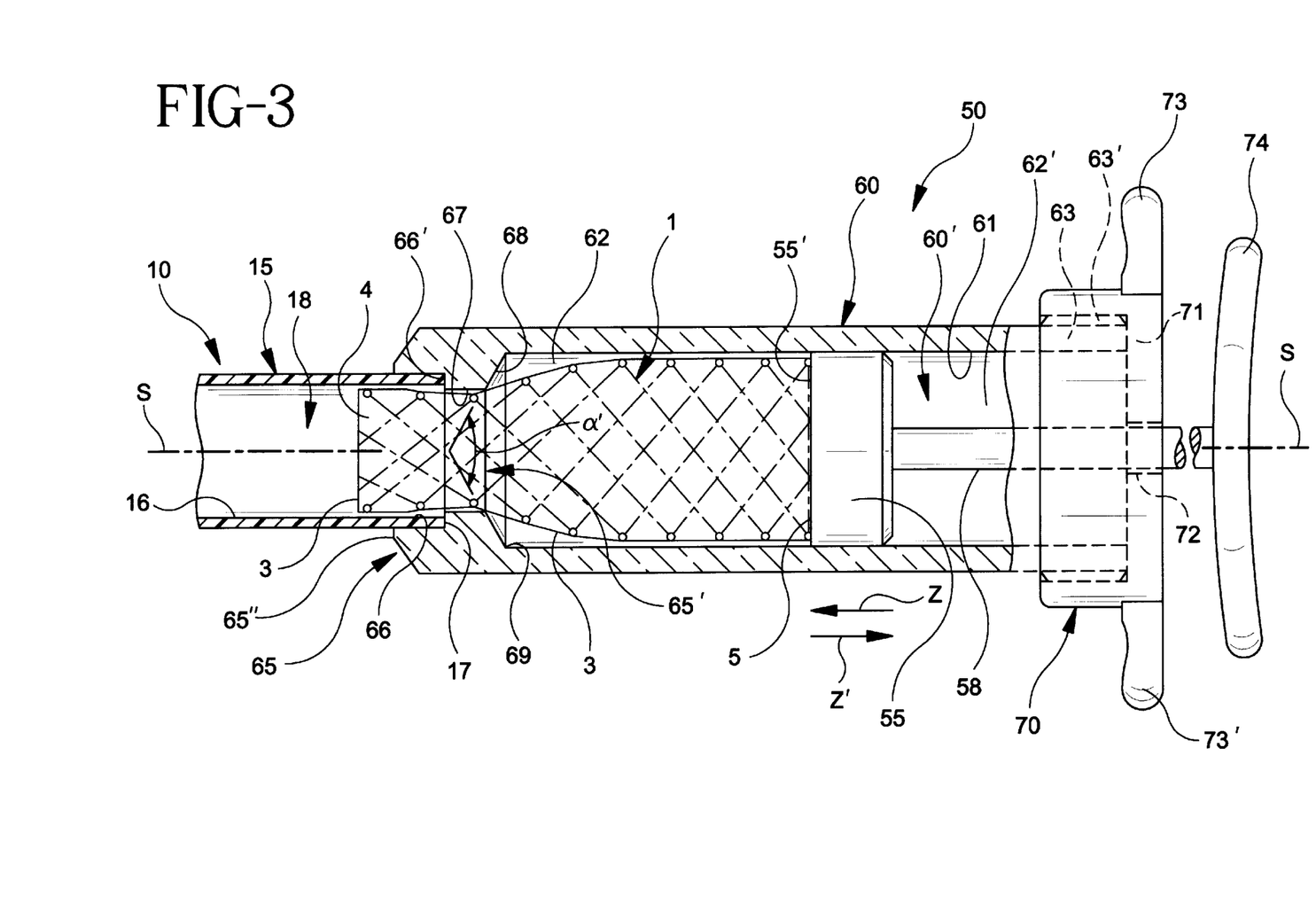
FIG. 3 a sectional view of a first embodiment of a device for introducing the endoprosthesis, of the type shown in FIG. 1, into the distal end section of a catheter.
Figure 6:
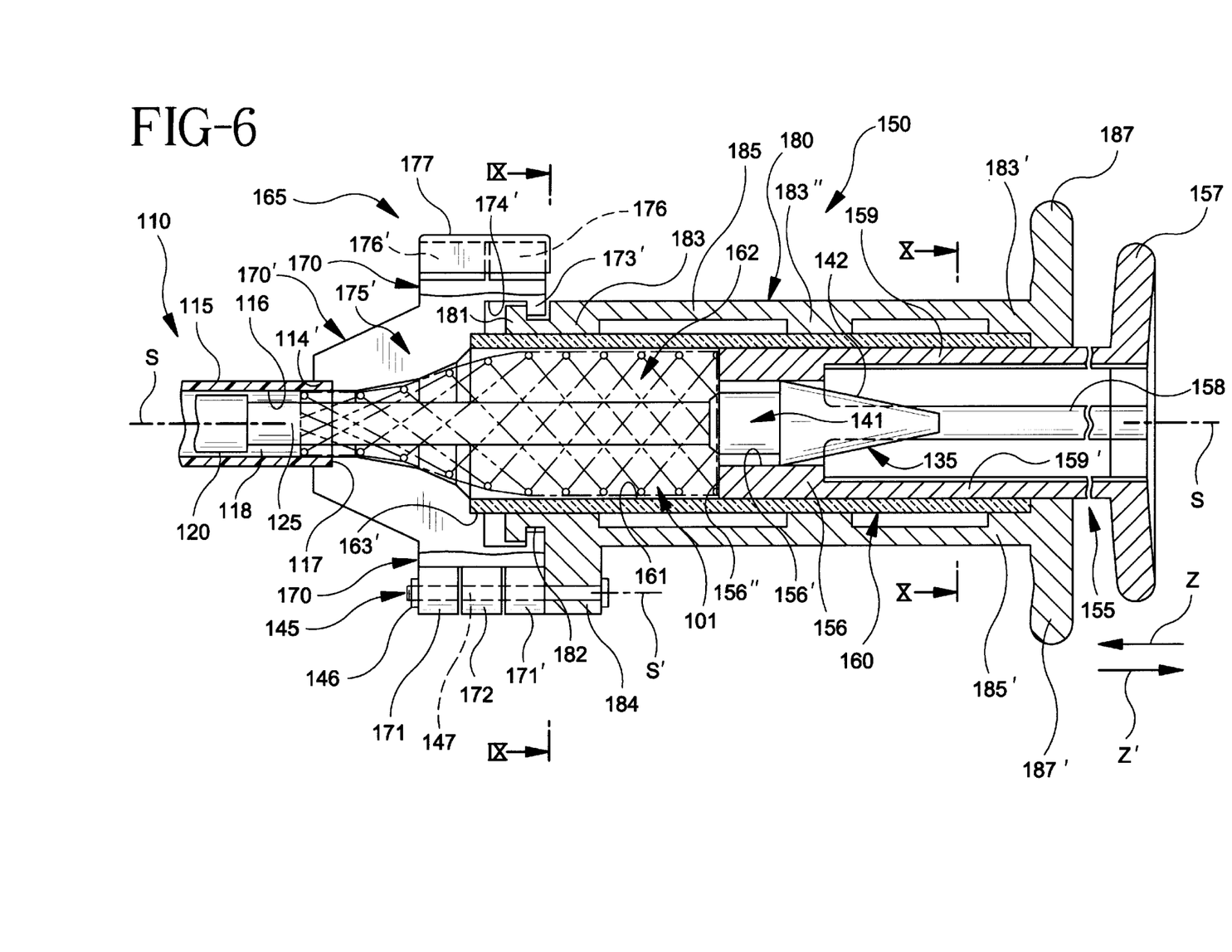
FIG. 6 a sectional view of a second embodiment of the device for introducing the endoprosthesis into the distal end section of a catheter.

The embodiment shown in FIG. 1 is a part of a tubular, self-expanding endoprosthesis in the expanded state, while in FIG. 2 this part is shown in a radially compressed and thus elongated state. Such an endoprosthesis is known for example from U.S. Pat. No. 4,655,771. In order to implant it in the vessel of a living creature, the endoprosthesis 1 is reduced in diameter and introduced into the distal end section of a catheter by means of a device according to the invention as illustrated in FIG. 3 or FIG. 6. The endoprosthesis 1, which is designed to be self-expanding in a known manner, consists substantially of a wire fabric 2 approximately helically wound around a theoretical central axis 6 (FIG. 1). The outer surface of the wire fabric 2 may additionally be provided with an extensible, diagrammatically depicted tubular sleeve 3. In the expanded state (FIG. 1), the endoprosthesis 1 has a first, larger diameter D, and in order to introduce the endoprosthesis 1 into the distal end section of the catheter it is reduced to a second, smaller diameter D' as shown in FIG. 2. The reduction in diameter of the endoprosthesis can, for example, be accomplished by applying relatively low tensile force at both ends 4 and 5 in the direction of the arrows 7 and 8. Once the two ends 4 and 5 are released, the endoprosthesis attempts to return to its original shape (FIG. 1), under its own elastic restoring force. In the expanded state, the wires are, for example, arranged at an oblique angle α in relation to each other in order to generate the highest possible radial supporting force.

FIG. 3 depicts a first embodiment of the invention and is a sectional view of the device 50. The device 50 is designed to insert or introduce an endoprosthesis 1, cut to the appropriate length and having a predetermined diameter D (FIG. 1), into a lumen 18 of an external catheter 15. The external catheter 15, whose distal end is inserted or introduced into a nose section 65 of the device 50, is part of a catheter designated in its entirety by reference number 10, said catheter being described in detail below in conjunction with FIG. 4.

The device 50, which in the embodiment illustrated in FIG. 3 has the form approximately of an injection syringe, comprises a hollow cylindrical housing 60 whose inner chamber 60' is substantially subdivided by a piston 55 arranged therein into a front chamber 62 for receiving the endoprosthesis 1 and a rear chamber 62'. The piston 55 can be displaced axially in the housing 60 in the direction of arrows Z or Z' by means of a piston rod 58 attached thereto and further by means of a, for example, disc-shaped handle element 74, attached to the end of the piston rod. The piston 55, which is guided at the inner surface 61 of the cylindrical inner space 60' so as to prevent tilting, is replaceably attached to the piston rod 58 by means not depicted, for example by a threaded connection.

At the rear end of the housing 60 there is provided an integrally formed shoulder 63 with an external thread 63' onto which shoulder is screwed a sealing cap 70 provided with an internal thread, which is not depicted. An opening 72 through which passes the piston rod 58 is provided in the rear wall 71 of the sealing cap 70. To permit better handling, grip elements 73,73' projecting radially outwards, and attached in a manner not depicted, are arranged on the threaded sealing cap 70. The grip elements 73 and 73' are appropriately arranged relative to the disc-shaped handle section 74 of the piston rod 58. The handle section 74, with the piston 55 arranged thereon, can be displaced in relation to the grip elements 73,73' in the direction of arrows Z or Z'.

As shown in FIG. 3, the nose section 65 arranged at the front end of the device 50 is provided with a recess 65' facing towards the front chamber 62, an opening 67 in communication therewith, as well as a recess 66. Starting from the end face 65" of the nose section 65, the recess 66 is bounded in the axial direction by an annular abutment surface 66' and is designed to receive the external catheter 15 (FIG.3) which is inserted as far as the abutment surface 66'.

Starting from the cylindrical inner wall 61 of the housing 60, the recess 65' of the nose section 65, said recess facing towards the front chamber 62, is designed as a slide wall 68, shaped like the edge of a plate and conically tapered in the direction of the opening 67. The recess 65', which is conically tapered at an angle α' in the direction of the opening 67, has substantially the form of a funnel through which the endoprosthesis 1, advanced by the piston 55, is forcibly reduced in size from the first larger diameter D (FIG. 1) to the smaller second diameter D' (FIG. 2), and then introduced into the lumen 18 of the outer catheter 15. The preferably oblique angle α' of the funnel-shaped recess 65' is approximately between 90° and 120° in size. In a variant not depicted here, it is possible for the slide wall 68 of the funnel-shaped recess 65', starting from the cylindrical inner wall 61 of the housing 60, to be approximately arcuately tapered in the direction of the opening 67.

In the first embodiment of the device 50 illustrated in FIG.3, with the sealing cap 70 unscrewed and the piston 55 removed, the endoprosthesis 1, which is to be inserted into the lumen 18 of the outer catheter 15, is loaded into the inner chamber 60' of the housing 60, then the piston 55 is inserted and the sealing cap is again screwed in place. The endoprosthesis 1 is in contact at its rear end 5 with the face 55' of the piston 55, and by moving the piston 55 in the direction of the arrow Z, the diameter of the opposite front end 4 of the endoprosthesis is reduced in size by the action of the slide wall 68 and, as diagrammatically illustrated in FIG.3, the endoprosthesis is forced through the opening 67 in the nose section 65 into the lumen 18 of the outer catheter 15. The sleeve 3 preferably provided at the outer periphery of the endoprosthesis 1 consists of a material having optimal sliding characteristics and thus brings about uniform reduction in diameter and introduction of the endoprosthesis 1 into the lumen 18 of the outer catheter 15. The endoprosthesis 1 is moved by the piston 55 in the direction of the arrow Z until the face 55' of the piston 55 comes into contact with the transitional point 69 formed between the cylindrical inner wall 61 and the inclined slide surface 68. Once the outer catheter has been removed from the device 50, the relatively short piece of the endoprosthesis 1 still projecting from the lumen is manually inserted into the outer catheter 15 and then the catheter 10 is fully assembled.

Figure 4:
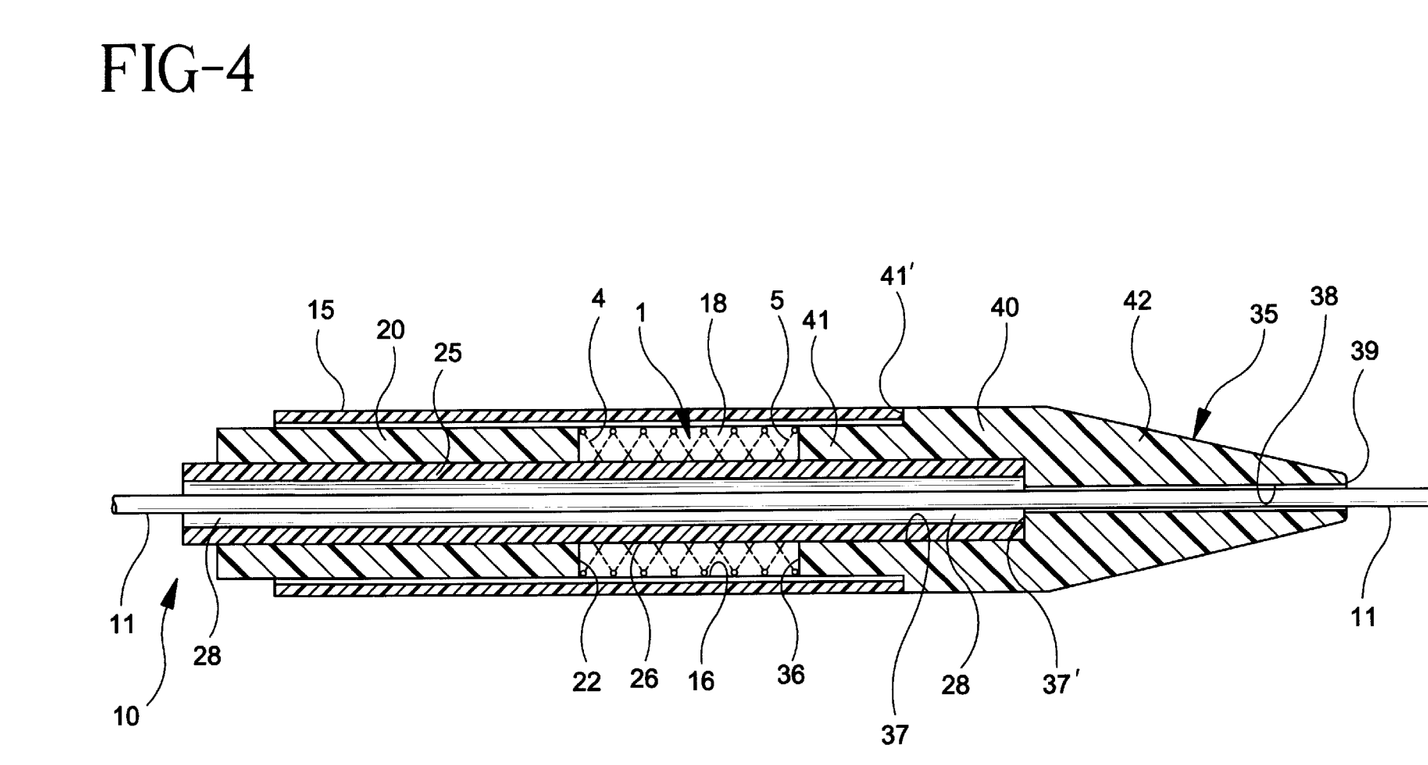
FIG. 4 a sectional view of the distal end section of the catheter, with the endoprosthesis introduced by means of the device depicted in FIG. 3.

FIG. 4 shows, on an enlarged scale, a general sectional view of the distal end section of the known catheter 10 with the endoprosthesis 1, which has been introduced into the lumen 18 of the outer catheter 15 by means of the device 50 (FIG.3). In the embodiment illustrated, the catheter 10 comprises the flexible outer catheter 15, an inner catheter 20, also of flexible design, coaxially arranged therein, as well as an inner shaft 25 coaxially arranged in said inner catheter. At the distal end of the flexible inner shaft 25 is arranged a catheter tip 35 which, for example, is attached by means of a suitable adhesive bond in a recess 37 in the catheter tip 35. The parts 35 and 25 form a structural unit that can be inserted or retracted axially into or out of the inner catheter 20.

The axially oriented lumen 18 for the endoprosthesis 1 to be inserted is provided between the cylindrical inner wall 16 of the outer catheter 15 and the cylindrical outer wall 26 of the free section of the inner shaft 25. In the assembled state, the endoprosthesis I is positioned with one end 4 at the end face 22 of the inner catheter 20 and with the other end 5 at the rear face 36 of the catheter tip 35.

At the distal end, the catheter tip 35 is provided with a part 42 which is conically tapered up to the end face 39, and adjoining this part there is a first cylindrical part 40 as well as, offset in relation thereto, a second cylindrical part 41 with an abutment surface 41'. Starting from the end face 39, the catheter tip 35 is provided with an axial bore 38 opening into the recess 37 of the catheter tip 35 or into the space 28 of the inner shaft 25. The catheter 10 may in addition be provided with a guide wire 11 passing axially through the inner shaft 25 and the catheter tip 35. The cylindrical part 41 is axially dimensioned such that in the assembled state a space (not indicated) corresponding approximately to the length of the compressed endoprosthesis 1 is provided between the end face 36 of the catheter tip 35 and the end face 22 of the inner catheter 20.

For the purpose of implanting the endoprosthesis 1, the catheter 10 is introduced in a known manner into a vessel, not depicted here, of a living creature. As soon as the appropriate point has been reached, the outer catheter 15 is retracted relative to the catheter tip 35, and as a result the endoprosthesis I expands under the action of its own elastic restoring force to the predetermined outer diameter and is released. Once the endoprosthesis 1 has been released and the outer catheter 15 has been pushed forward onto the cylindrical part 41 of the catheter tip 35, the catheter 10 can be removed from the vessel.

Figure 5:
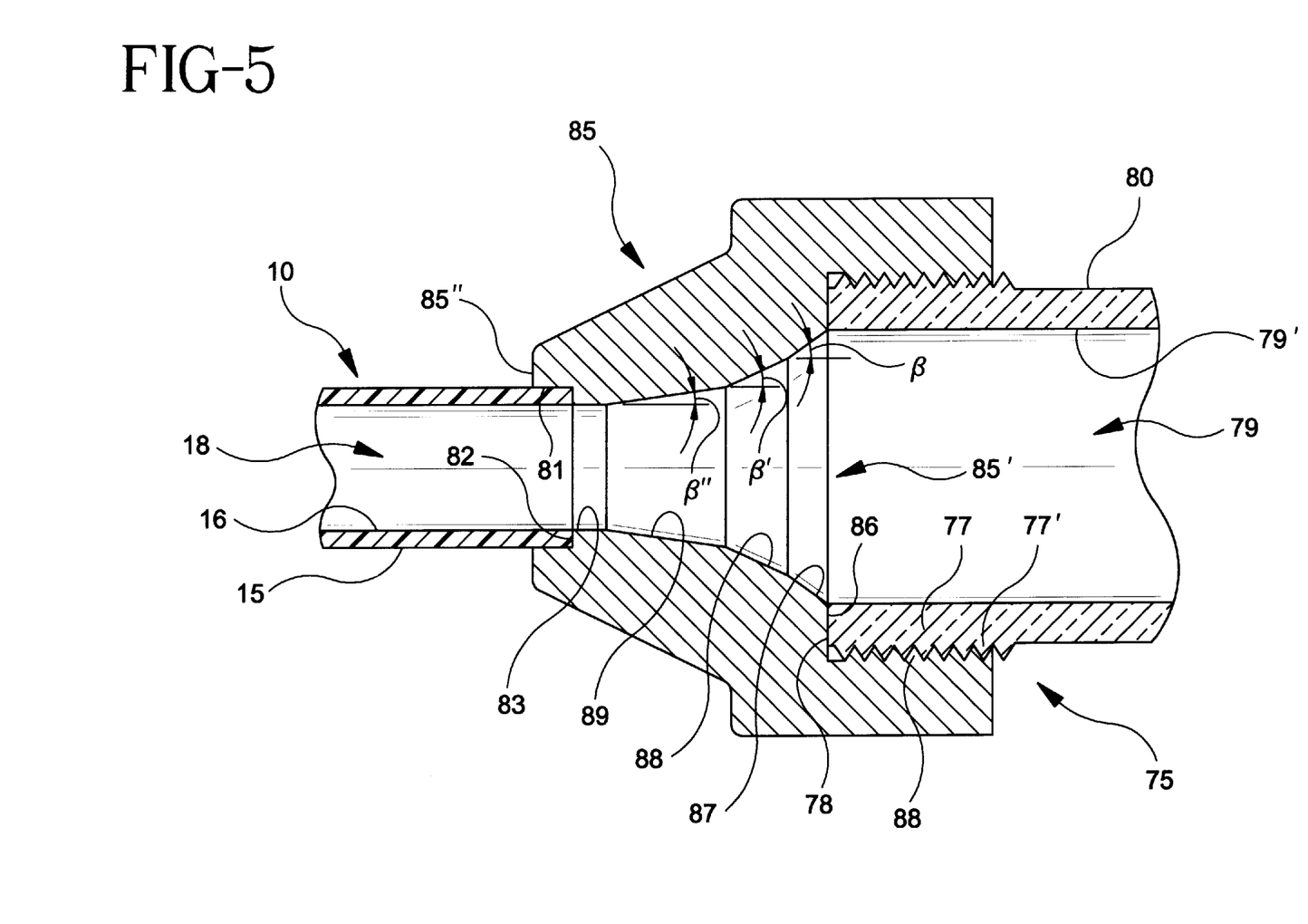
FIG. 5 a sectional view of a variant of a nose section for the device depicted in FIG. 3.

FIG. 5 shows a second embodiment of the invention, namely a device 75 with part of the cylindrical housing 80, but without the piston 55 displaceably arranged therein. Unlike the embodiment illustrated in FIG.3, the housing 80 is provided at its front end with a shoulder 77 and an external thread 77' onto which is screwed a nose section 85 provided with an internal thread 88. The nose section 85, which is provided with an abutment surface 86, is screwed onto the housing 80, all the way up to the end face 78. A recess 81, stepped in relation to an opening 83, is provided at the end face 85" of the nose section 85, said recess being bounded in the axial direction by an annular abutment surface 82. The recess 81 serves to receive the outer catheter 15 which is inserted up to the abutment surface 82. In this embodiment, the hollow cylindrical front chamber 79 of the housing 80 is in communication with the opening 83 and the lumen 18 of the outer catheter 15 via a multiply stepped and substantially funnel-shaped recess 85'.

For the purpose of introducing the endoprosthesis 1 (FIG.3), the recess 85' provided in the nose section 85 and adjoining the cylindrical inner wall 79' of the housing 80 is provided, for example, with a first slide surface 87, a second slide surface 88 adjoining thereto, and a third slide surface 89 adjoining thereto, and the said third slide surface 89 opens into the cylindrical opening 83. In the funnel-shaped recess 85', which is axially oriented in relation to the nose section 85, the first slide surface 87 is conically tapered at a first angle $\beta$ in the direction of the second slide surface 88, and the latter is conically tapered at a second angle $\beta'$ in the direction of the third slide surface 89, and the latter is conically tapered at a third angle $\beta''$ in the direction of the cylindrical opening 83. In the embodiment of the funnel-shaped recess 85' shown in FIG. 5, the first angle $\beta$, is larger than the second angle $\beta'$ and the latter is larger than the third angle $\beta''$. The special design of the recess 85' in the nose section 85 ensures successive reduction in diameter of the endoprosthesis 1 (FIG. 1) which is supplied and introduced into the lumen 18 of the outer catheter 15.

With the device 75 shown in FIG. 5, it is advantageously possible to screw a nose section 85 onto the outer thread 77' of the housing 80 as a function of the respective endoprosthesis which is to be introduced, said housing possessing an appropriately funnel-shaped recess 85' as a function of the endoprosthesis.

At this point it should be mentioned that the cylindrical housing 60 with the nose section 65 (FIG.3), or the cylindrical housing 80 with the screw-on nose section 85 (FIG. 5), as well as a cylindrical housing 160 described below having a two-part nose section 165 or 195, are preferably manufactured from a transparent material.

FIG. 6 shows a diagrammatical cross section through a second embodiment, namely device 150, for inserting or introducing the endoprosthesis 101, cut to an appropriate predetermined length, into the lumen 118 of a catheter 110. The endoprosthesis 101 is, for example, similar in design to the embodiment of endoprosthesis 1 shown in FIG. 1 and FIG. 2, but other design variants of the endoprosthesis may also be used.

Device 150 comprises a frame-like receiving body 180, the housing 160 arranged and supported therein, a piston unit 155 which can be moved back and forth along the longitudinal axis S—S in the housing 160, as well as the nose section denoted in its entirety by the reference number 165. The nose section 165 possesses two parts 170 and 170' which, in the embodiment illustrated, are separated from each other vertically in the plane of symmetry, and these two parts are connected to each other and mounted on the receiving body 180 via a joint 145 arranged at a distance from the theoretical longitudinal axis S—S. The parts 170 and 170' are preferably lockable with one another by means of a locking element 177 arranged, for example, opposite the joint 145.

The receiving body 180 has two axially oriented, peripherally oppositely arranged longitudinal members 185 and 185' which are connected with one another at the front end by a first circular support element 183 and at the rear end by a second circular support element 183'. Preferably in the axial direction, approximately in the middle of the receiving body 180, a segment-shaped support element 183" is additionally provided for the housing 160. At least two oppositely arranged grip elements 187 and 187' are, for example, integrally formed on the second support element 183'. The purpose of the individual support elements 183, 183' and 183" is substantially to receive and coaxially mount the housing 160 in the receiving body 180. The housing 160 is manufactured at least partially but preferably totally from transparent material.

Figure 8:
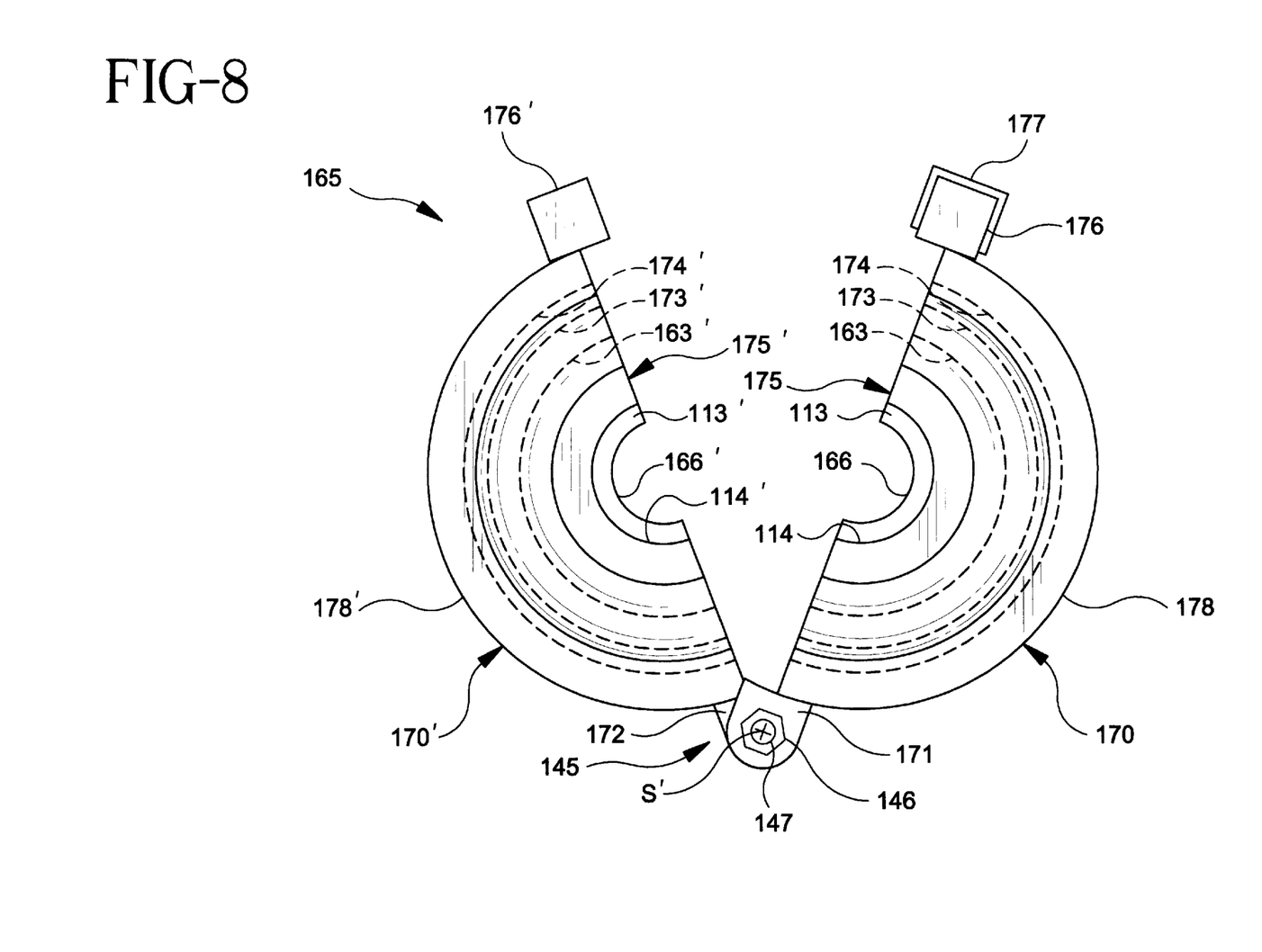
FIG. 8 an elevational view in the direction of arrow A of the nose section as shown in FIG. 7, with the two parts pivoted open relative to each other along a separation line to permit introduction of the catheter.

The nose section 165 arranged at the other end of the device 150 and facing the distal end of the catheter 110 comprises the two parts 170 and 170', which can be pivoted open relative to each other and which are mounted on a bracket 184 attached to the receiving body 180, around a common axis S' running parallel to the longitudinal axis S—S. The two approximately shell-shaped parts 170 and 170' are pivotably mounted relative to each other on the bracket 184 of the receiving body 180 by means of integrally formed hinge elements 171 and 171' or 172 via a threaded bolt 147 with a nut 146 screwed thereon (FIG. 8). The individual elements 146,147,171,171',172 together form the join referred to in its entirety by the reference number 145.

At the side facing the receiving body 180, the two shell-shaped parts 170 and 170' are each provided with an integrally formed semicircular annular element 173 and 173'. When both parts 170 and 170' are pivoted together in the closed position, the two annular elements 173 and 173', as illustrated in FIG. 6, are arranged in an annular groove 182 of the receiving body 180, and a ring 181 of the receiving body 180 is arranged in an annular groove 174, 174' of the parts 170 and 170'. In this position, the cylindrical body 160 is arranged in a recess 163,163' of both shell-shaped parts 170 and 170' of the nose section 165. Both parts 170 and 170' are provided with projecting elements 176 and 176' arranged on the outer diameter and may be locked together with each other by means of the locking element 177 that can be brought into engagement with these projecting elements.

Deviating from the first embodiment according to FIG. 3, it is possible, as already mentioned, in the second embodiment according to FIG. 6, for the nose section 165, which is articulatedly attached to the frame-shaped receiving body 180 and which is also provided with the two parts 170 and 170' which are pivotable in relation to each other around the S' axis, to be pivoted open transversely to the theoretical longitudinal axis S—S of the device 150. With the two parts 170 and 170' pivoted open, the endoprosthesis 101 can, for example, be introduced in the fully expanded state into the space 162 of the housing 160. Next, the catheter 110, comprising the elements 115,120,125 and 135 (FIG. 6) is inserted as a structural unit in a first phase in the radial direction between the two parts 170 and 170' (FIG. 8) of the nose section 165, and then it is introduced axially into the housing 160 of the device 150. Once the endoprosthesis 101 and the catheter 110 are arranged in the housing 160, the parts 170 and 170' of the nose section 165 are pivoted shut once more and locked together by means of the locking element 177 (FIG. 6).

In this embodiment, the catheter 110 is located in the assembled position together with the outer catheter 115 in an annular recess 114,114' of the nose section 165, and the catheter tip 135 which is arranged on the inner shaft 125, and also passes through the front chamber 162, is preferably operatively connected with a piston 156 of the piston unit 155 which is located in the housing 160 of the device 150 and which can be moved in the direction of the arrow Z or Z' along the longitudinal axis S—S.

The piston unit 155 comprises the piston 156 provided with an opening 156', as well as arms 158,158' and 159,159' integrally formed thereon and oriented in the direction of the longitudinal axis S—S. The piston unit 155 is guided in the direction of the longitudinal axis S—S by means of the members 158,158' and 159,159' arranged opposite each other around the periphery of the inner wall 161 of the housing 160. At the outer end opposite the piston 156 the arms 158,158' and 159,159' are attached, in a manner not shown in detail here, to a substantially disc-shaped handle element 157. Deviating from the embodiment illustrated in FIG. 3, in the embodiment shown in FIG. 6, as mentioned above, when the parts 170,170' of the nose section 165 are pivoted open, the endoprosthesis 101 can be fully introduced, i.e. in the assembled state, into the housing 160.

In order to introduce the endoprosthesis 101 into the lumen 118 of the outer catheter 115, the piston unit 155 with the handle element 157 is displaced in the direction of the arrow Z. By moving the piston unit 155 in the direction indicated by the arrow Z, the endoprosthesis 101 is forced through an approximately funnel-shaped recess 165' in the nose section 165, as partially illustrated in FIG. 6, into the cylindrical space 118 of the outer catheter 115. As soon as the end face 156" of the piston 156 of the piston unit 155 comes into engagement with the recess 165' of the nose section 165, the piston unit is retracted preferably in the direction of arrow Z' and then the nose section 165 is opened by pivoting open the two parts 170 and 170' to remove the catheter 110. Next, the catheter tip 135 with the inner shaft 125 and the integrally formed cylindrical part 141, is manually inserted into the lumen 118 of the outer catheter 115.

In a variant not shown here, it also possible, however, when the piston unit 155 is pushed in the direction of the arrow Z, for the catheter tip 135 with the inner shaft 125 to be moved simultaneously in the direction of the arrow Z. As a result, the cylindrical part 141 of the catheter tip 135 can be directly inserted into the lumen 118 of the outer catheter 115. In order to achieve simultaneous movement of the piston unit 155, of the catheter tip 135 and of the inner shaft 125, the opening 156' is provided, for example, with a stop—not shown here—which engages with the conical part 142 of the catheter tip 135 and thus can be simultaneously moved with the piston unit 135 in the direction of arrow Z (FIG. 6).

Figure 7:
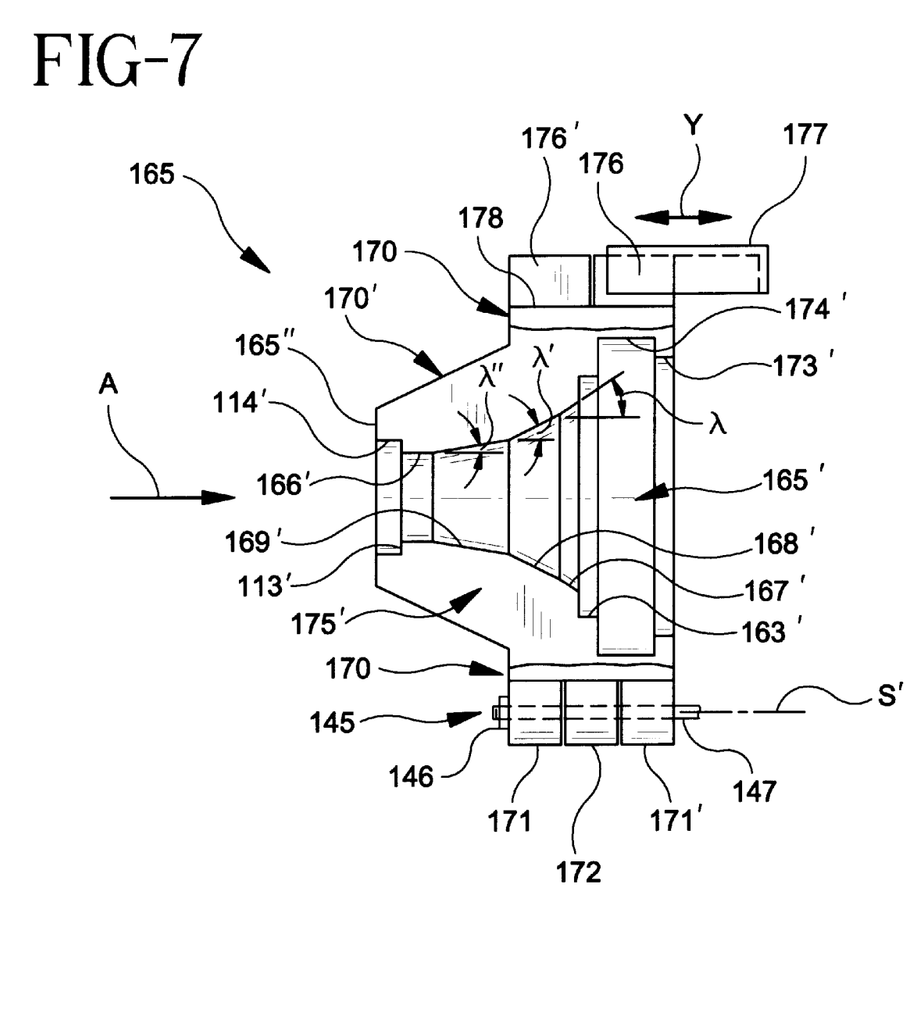
FIG. 7 a lateral view taken along a separation plane of a nose section provided with two articulatedly connected parts, for the device shown in FIG. 6.

FIG. 7 is a view taken along the separation plane of the nose section 165 for the device 150 illustrated in FIG. 6, showing the surface 175' of the part 170', an elevational view of the locking element 177 arranged in the upper area of the nose section, together with the associated projecting elements 176 and 176', and an elevational view of the joint 145 having the individual parts 146,147 and 171,171' as well as 172 arranged in the lower area of the nose section.

FIG. 8 shows the nose section 165 in lateral view according to the direction of the arrow A in FIG. 7, as well as pivoted open along the theoretical plane of separation. The two parts 170 and 170' are shown partially pivoted open around the axis S' of the joint 145 to permit insertion of the catheter 110 (FIG. 4). In addition, FIG. 8 shows the projecting elements 176 and 176' arranged on the circular surface 178 and 178' of the two parts 170 and 170' as well as the, in profile cross section, approximately U-shaped locking element 177. The locking element 177 is, for example, slidingly arranged in the direction of the double arrow Y (FIG. 7) on one of the projecting elements 176 of the first part 170 and can be brought into engagement with the other projecting element of the second part 170' so that the nose section 165 forms a unit when the surfaces 175,175' of the two parts 170 and 170' are in abutment.

As shown in FIG. 7 and FIG. 8, the nose section 165 with the two parts 170,170' is further provided with the funnel-shaped recess 165' for introducing the endoprosthesis 101 into the lumen 118 of the outer catheter 115 (FIG. 6). The recess 165' is in communication via an opening 166,166' with the lumen 118 of the outer catheter 115, which is not depicted in FIG. 7 and FIG. 8. The funnel-shaped recess comprises, for example, a first slide surface 167,167', an adjoining second slide surface 168,168' as well as a third slide surface 169,169', and said third slide surface 169,169' opens into the opening 166,166'. The slide surfaces 167, 168,169 provided on the part 170 and the opening 166 are indicated in FIG. 8.

In the case of the funnel-shaped recess 165' oriented in the axial direction of the nose section 165, the first slide surface 167,167' is conically tapered in the direction of the second slide surface 168,168' at a first angle λ, and this second slide surface is conically tapered in the direction of the third slide surface 169,169' at a second angle λ', and the third slide surface is conically tapered in the direction of the cylindrical opening 166,166' at a third angle λ". In the embodiment illustrated (FIG. 7), the first angle λ is preferably larger than the second angle λ' which in turn is preferably larger than the third angle λ". Furthermore, a recess 114 bordered by an annular abutment surface 113,113' is provided at the end face 165" of the nose section 165 for the purpose of inserting or connecting the outer catheter 115 (FIG. 6) The two parts 170,170' of the nose section 165 are furthermore provided with a first annular recess 163,163' for the housing 160 and with the second annular recess 174,174' for receiving the stop ring 181 integrally formed on the receiving body 180, and they are also provided with the annular section 173,173' which, in the assembled state, engages in the annular groove 182 in the receiving body 180 (FIG. 6).

Figure 9:
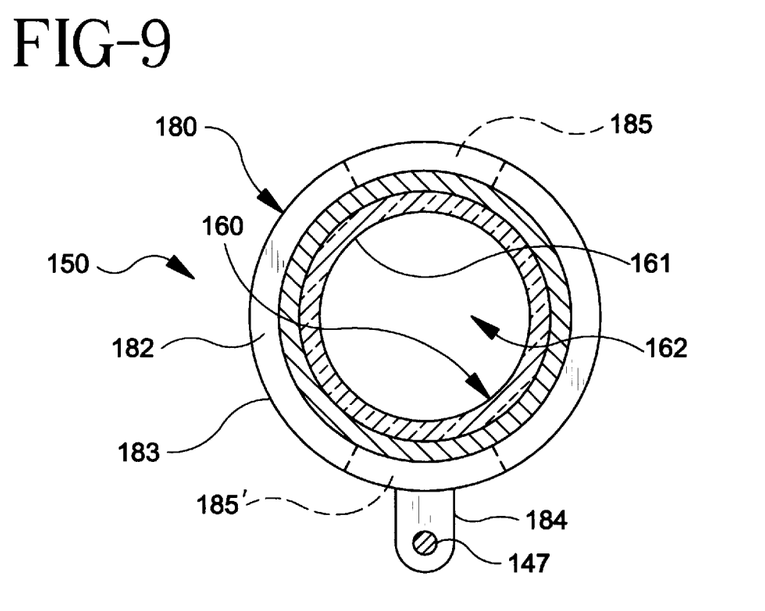
FIG. 9 a sectional view of the device according to FIG. 6, taken along the line IX—IX.

FIG. 9 is a sectional view of the device 150 taken along the line IX—IX in FIG. 6, showing the housing 160, which is coaxially mounted in the support elements 183,183' and 183" of the receiving body 180. On the support element 183 facing the nose section 165 there is integrally formed the bracket 184 on which the two parts 170 and 170' of the nose section 165 are mounted by means of the joint 145 so as to be pivotable transversely to the longitudinal axis S—S of the device 150 (FIG. 8).

Figure 10:
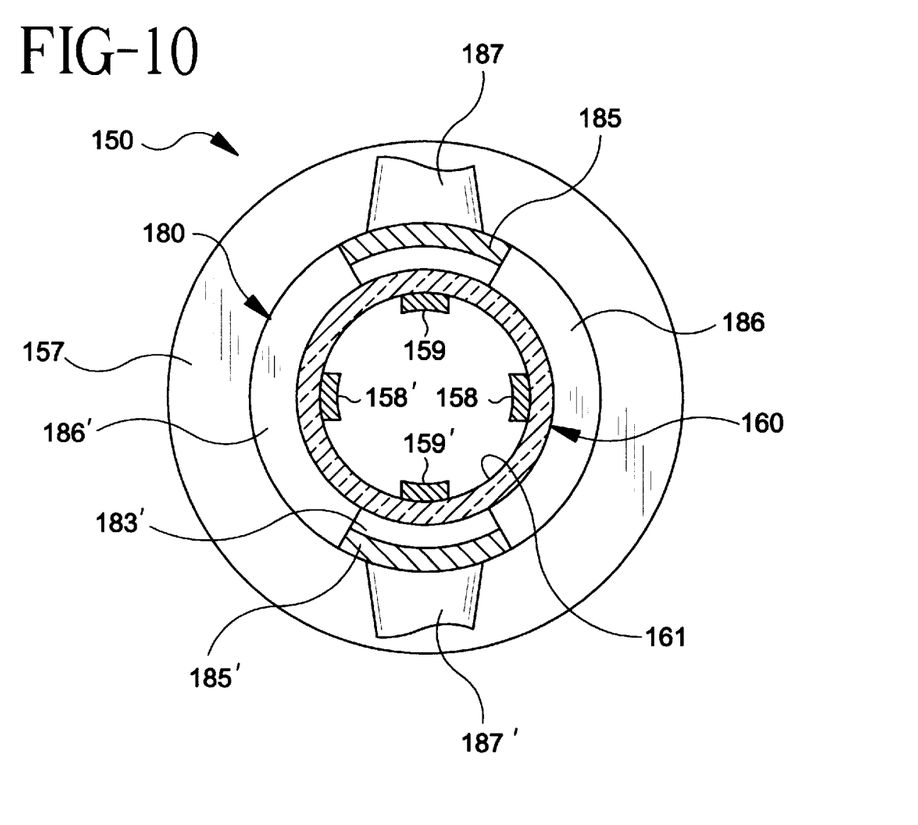
FIG. 10 a sectional view of the device according to FIG. 6, taken along the line X—X.

FIG. 10 is a sectional view of the device 150 taken along the line X—X in FIG. 6, showing the cylindrical body 160 mounted between the two diametrically oppositely arranged and approximately arcuate, segment-shaped longitudinal members 185 and 185' of the receiving body 180. The FIG. 10 furthermore shows the axially oriented, diametrically oppositely arranged arms 158,158' and 159,159' of the piston unit 155, said arms being in contact with the inner wall 161 of the cylindrical body 160 (FIG. 6). The two oppositely located and here only partially depicted grip elements 187 and 187' are arranged on the longitudinal members 185 and 185' of the receiving body 180. The, for example, disc-shaped handle element 157 of the piston unit 155 can also be seen in FIG. 10.

Figure 11:
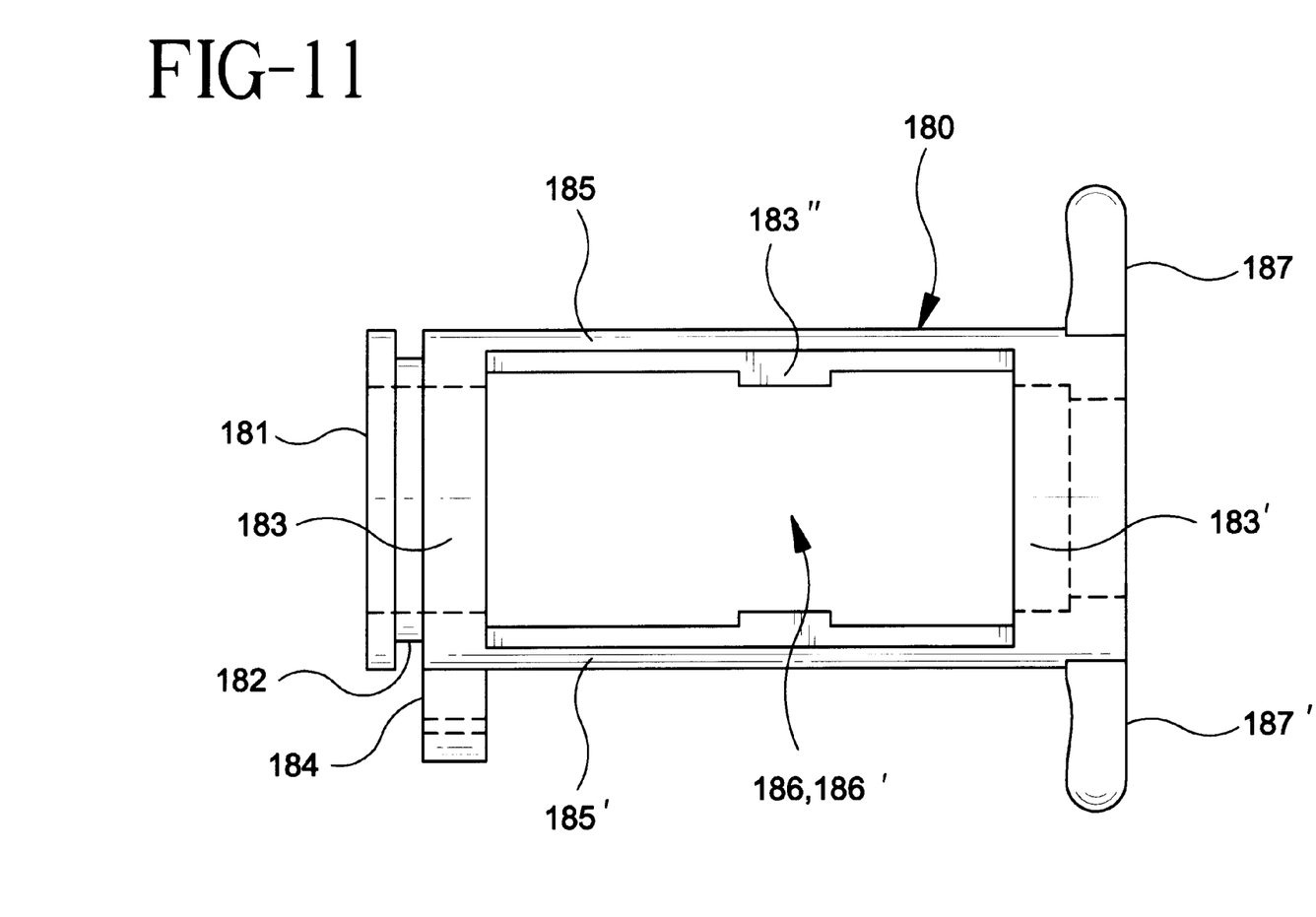
FIG. 11 a smaller scale elevational view of a receiving body for a cylindrical body, with a piston unit arranged therein, for the device according to FIG. 6.

FIG. 11 is an elevational view of the receiving body 180 of the device 150 showing the two grip elements 187 and 187' arranged at the one end of the second support element 183', as well as the two longitudinal members 185 and 185' which are linked with each other at the other end by the second support element 183. The second support element 183 is provided with the outer annular groove 182 and the stop ring 181 as well as the integrally formed bracket 184. The two longitudinal members 185 and 185' of the receiving body 180, which are arranged between the support elements 183,183' and 183", are designed in such a way that in the peripheral direction, two oppositely arranged windows are provided in the form of axially oriented openings 186 and 186'.

Figure 12:
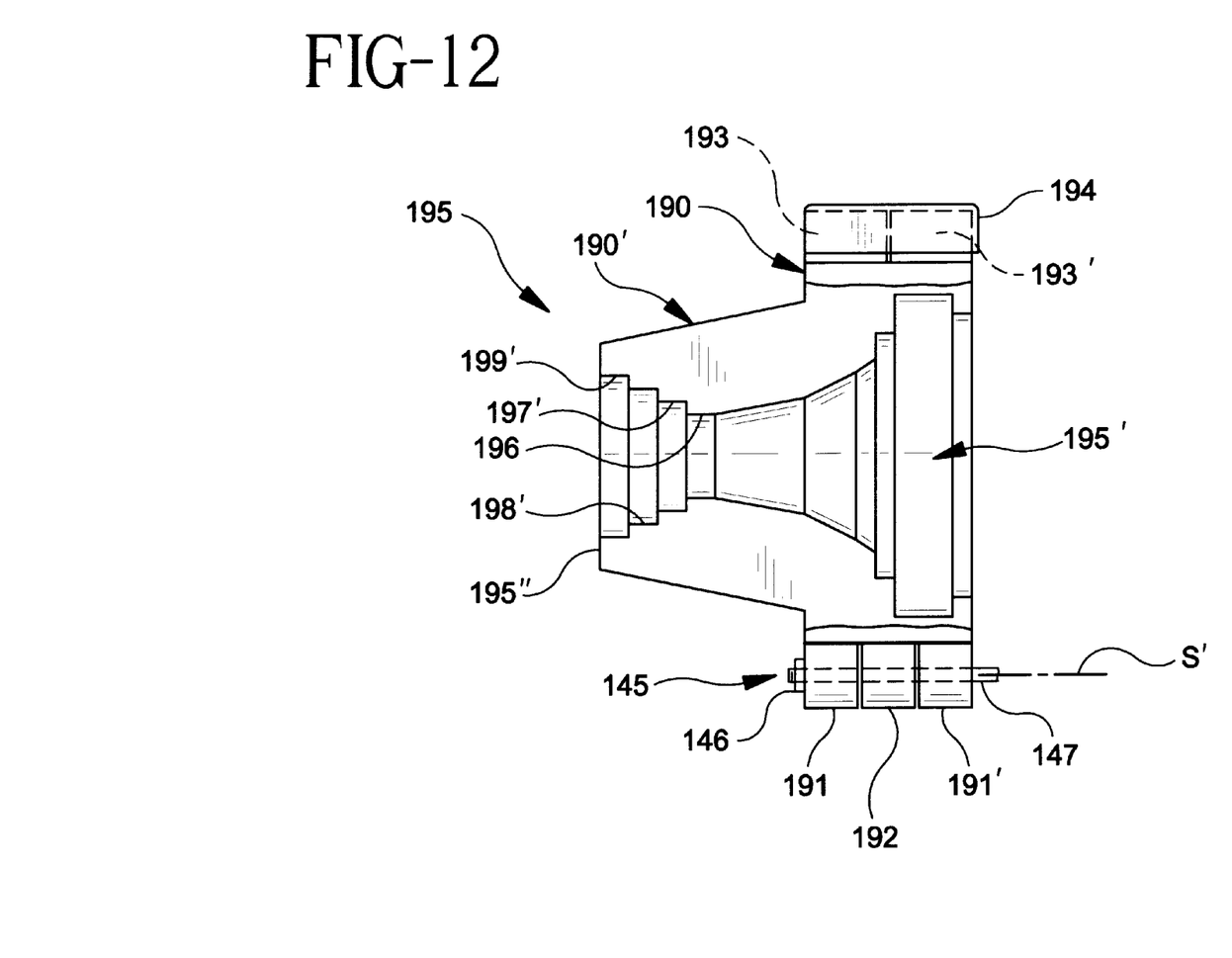
FIG. 12 a lateral view taken along the separation plane of a variant of the nose section, provided with two articulatedly connected parts, for the device according to FIG. 6.

FIG. 12 depicts a variant of the nose section 195 for the device 150 shown in FIG. 6, said nose section possessing a recess 195' and comprising the two parts 190 and 190', with the projecting elements 193,193' and the associated locking element 194 arranged on the outer periphery thereof, and the individual oppositely arranged elements 146,147,191,191' and 192 of the joint 145. The recess 195' provided in the nose section 195 is, for example, similar in design to the recess 165' of the nose section 165 shown in FIG. 7 and FIG. 8.

Deviating from nose section 165, the nose section 195 shown in FIG. 12 is provided at the end face 195" with several recesses of different diameter designed to receive differently formed outer catheters. FIG. 12 shows the recesses 197',198' and 199' arranged in part 190', said recesses corresponding with the recesses (not depicted) arranged in the other part 190 of the nose section 195. The recesses are in each case designed to receive an outer catheter 115 having an appropriately dimensioned outer diameter (FIG. 6).

The invention is not limited to the above-described embodiments of the device 50 with the nose section 65 or 85, nor is it restricted to the device 150 with the nose section 165, or to the embodiment of the nose section 195. Further advantageous embodiments of the devices 50 and 150, which are designed for the introduction of an elongated catheter, especially a catheter in the assembled state, may also be used. The device may also be designed in such a way that two shell-shaped parts separated longitudinally are operatively connected with one another at the proximal end of the device such that they can be pivoted open to receive the catheter, and at the distal end they are lockable by suitable means. With a device of this kind, the catheter can be inserted into the device as a structural unit together with the outer catheter, which is retracted relative to the catheter tip, and then the correspondingly designed endoprosthesis can be introduced into the outer catheter.

By means of the device 50 or 150 according to the invention it is possible to load appropriately designed endoprostheses into customary commercial catheters which are introduced into a vessel for the purpose of implanting the endoprosthesis. Device 150 is regarded as particularly advantageous because in this case the fully assembled catheter can be loaded with the endoprosthesis.

Various modifications and changes in detail may be made to the above-described embodiments and examples without departing from the spirit and scope of the invention. It is therefore intended that all such matter as described in the foregoing description and shown in the attached drawings be considered as illustrative only and not limiting. All documents cited herein, including the cited patent application, are incorporated by reference herein in their entireties for all purposes.

I claim:

1. A device for introducing a tubular, self-expanding endoprosthesis into a catheter shaft, the device comprising:
    a housing for receiving the endoprosthesis;
    a piston unit having an axis coaxially aligned with an axis of the catheter shaft for axially displacing the endoprosthesis relative to the shaft; and
    a tapering outlet opening in the housing for radially compressing the endoprosthesis.

2. The device of claim 1 wherein the housing further comprises a hollow cylinder having an axis, said piston unit within the cylinder and displaceable along the axis of the cylinder, and an outlet opening arranged coaxially to the axis of the cylinder.

3. The device of claim 1 wherein the outlet opening has the form of a truncated cone.

4. The device of claim 3 wherein the truncated cone possesses an oblique angle.

5. The device of claim 1 wherein the outlet opening has the form of a series of adjacent truncated cones.

6. The device of claim 1 wherein the outlet opening has the form of a hyperboloidal section.

7. The device of claim 1 wherein the outlet opening is arranged in a replaceable nose section of the housing.

8. The device of claim 7 wherein the nose section of the housing is replaceable by virtue of being provided with a threaded connection.

9. The device of claim 7 wherein the nose section is divisible.

10. The device of claim 9 wherein the nose section possesses two parts connected by a joint, said parts being pivotable between an open, replacement position and a closed, locking position.

11. The device of claim 10 wherein the parts are lockable in the closed position to fasten them on the housing.

12. The device of claim 1 wherein the piston unit is annular in shape and has an axial recess.

13. The device of claim 1 wherein the housing possesses a connecting opening, arranged coaxially to the outlet opening, for receiving an end section of the catheter shaft.

14. The device of claim 13 wherein the outlet opening possesses several sections with stepped diameters.

15. The device of claim 1 wherein the housing is made at least partially of transparent material.

16. The device of claim 1 wherein the housing may be opened laterally in relation to the direction of movement of the piston unit to receive the endoprosthesis.

17. The device of claim 1 wherein the piston unit may be removed from the housing in order to receive the endoprosthesis.

* * * * *